(12) United States Patent
Wätzig et al.

(10) Patent No.: US 9,034,817 B2
(45) Date of Patent: May 19, 2015

(54) SGP130/FC DIMERS FOR TREATMENT OF INFLAMMATORY DISEASE

(71) Applicant: Conaris Research Institute AG, Kiel (DE)

(72) Inventors: Georg H. Wätzig, Kiel (DE); Dirk Seegert, Altenholz (DE)

(73) Assignee: CONARIS RESEARCH INSTITUTE AG, Kiel (DE)

( * ) Notice: Subject to any disclaimer, the term of this patent is extended or adjusted under 35 U.S.C. 154(b) by 0 days.

(21) Appl. No.: 14/109,466

(22) Filed: Dec. 17, 2013

(65) Prior Publication Data

US 2014/0178378 A1 Jun. 26, 2014

Related U.S. Application Data

(62) Division of application No. 12/307,003, filed as application No. PCT/EP2007/005812 on Jun. 29, 2007, now Pat. No. 8,895,012.

(30) Foreign Application Priority Data

Jun. 30, 2006 (EP) ..................................... 06013668

(51) Int. Cl.
| | |
|---|---|
| *A61K 38/16* | (2006.01) |
| *C07K 16/24* | (2006.01) |
| *A61K 38/20* | (2006.01) |
| *C07K 14/715* | (2006.01) |

(52) U.S. Cl.
CPC .............. *C07K 16/248* (2013.01); *A61K 38/204* (2013.01); *C07K 14/7155* (2013.01); *C07K 2319/30* (2013.01)

(58) Field of Classification Search
CPC .................................................... A61K 38/204
USPC ........................................ 514/1.1, 18.7, 21.2
See application file for complete search history.

(56) References Cited

U.S. PATENT DOCUMENTS

| | | | |
|---|---|---|---|
| 4,751,180 | A | 6/1988 | Cousens et al. |
| 5,457,035 | A | 10/1995 | Baum et al. |
| 5,783,672 | A | 7/1998 | Mosley et al. |
| 6,605,703 | B1 | 8/2003 | Schaeffer et al. |
| 6,838,076 | B2 | 1/2005 | Patton et al. |
| 6,887,687 | B2 | 5/2005 | Anderson |
| 7,534,862 | B2 | 5/2009 | Seegert et al. |
| 7,629,147 | B2 | 12/2009 | Seegert et al. |
| 7,851,182 | B2 | 12/2010 | Seegert et al. |
| 2002/0012962 | A1 | 1/2002 | Stahl et al. |
| 2003/0118510 | A1 | 6/2003 | Patton et al. |
| 2007/0270334 | A1 | 11/2007 | Seegert et al. |
| 2008/0227155 | A1 | 9/2008 | Seegert et al. |

FOREIGN PATENT DOCUMENTS

| | | |
|---|---|---|
| DE | 19941897 A1 | 3/2001 |
| EP | 0442724 A2 | 8/1991 |
| EP | 1148065 A1 | 10/2001 |
| EP | 1491554 A1 | 12/2004 |
| EP | 1801121 A1 | 6/2007 |
| WO | WO-9412520 A1 | 6/1994 |
| WO | WO-9533059 A2 | 12/1995 |
| WO | WO-0158957 A2 | 8/2001 |
| WO | WO-03008454 A2 | 1/2003 |
| WO | WO-2004113383 A2 | 12/2004 |
| WO | WO-2006021453 A2 | 3/2006 |

OTHER PUBLICATIONS

Lund et al., Human FcγRI and FcγRII Interact with Distinct But Overlapping Sites on Human IgG$^1$, Journal of Immunology, 147(8):2657-2662 (1991).
Hammer et al., Increased inflammation and lethality of *Dusp1$^{-/-}$* mice in plymicrobial peritonitis models, Immunology, 131:395-404 (2010).
Lee et al., Interleukin-6 Induces S100A9 Expression in Colonic Epithelial Cell through STAT3 Activation in Experimental Ulcerative Colitis, PLoS ONE, 7(9):e38801. doi:10.1371/journal.pone. 0038801 (2012).
Tenhumberg et al., Structure-guided Optimization of the Interleukin-6 Trans-signaling Antagonist spg130, J. Biol. Chem., 283:27200-27207 (2008).
Ancey et al., A fusion protein of the gp130 and interleukin-6Ralpha ligangbinding domains acts as a potent interleukin-6 inhibitor, J. Biol. Chem., 278(19):16968-16972 (2003).
Atreya et al., Blockade of interleukin 6 trans signaling suppresses T-cell resistance against apoptosis in chronic intestinal inflammation: Evidence in Crohn disease and experimental colitis in vivo, Nature Medicine, 6(5):583-588 (2000).
Barkhausen et al., Selective blockade of interleukin-6 trans-signaling improves survival in a murine polymicrobial sepsis model, Crit. Care Med., 39(6):1407-1413 (2011).
Bayliss et al., A humanized anti-IL-6 antibody (ALD518) in non-small cell lung cancer, Expert Opin. Viol. Ther. Early Online, pp. 1-6 (Oct. 17, 2011).
Becker et al., TGF-βSuppresses Tumor Progression in Colon Cancer by Inhibition of IL-6 trans-Signaling, Immunity, 21:491-501 (2004).
Bitter et al., Expression and Secretion Vectors for Yeast, Methods in Enzymology, 153:515:545 (1987).

(Continued)

*Primary Examiner* — Prema Mertz
(74) *Attorney, Agent, or Firm* — Choate, Hall & Stewart LLP; Brenda H. Jarrell; Rolando Medina

(57) ABSTRACT

Described are polypeptide dimers comprising two soluble gp130 molecules wherein each of said molecules is fused to an Fc domain of an IgG1 protein and wherein the hinge region of the Fc domain is modified resulting in advantageous properties of the dimer. In a particularly preferred embodiment, the hinge region comprises the amino acid sequence motif $Ala_{234}$-$Glu_{235}$-$Gly_{236}$-$Ala_{237}$. Moreover, a pharmaceutical composition containing said dimer and various medical uses are described.

9 Claims, 3 Drawing Sheets

(56) References Cited

OTHER PUBLICATIONS

Boulanger et al., Hexameric Structure and Assembly of the Interleukin-6/IL-6 α-Receptor/gp130 Complex, Science 300:2101-2104 (2003).

Boulanger et al., Materials & Methods, 5 pages (2003).

Broglie et al., Light-Regulated Expression of a Pa Ribulose-1,5-Bisphosphate Carboxylase Small Subunit Gene in Transformed Plant Cells, Science, 224:838-843 (1984).

Canfield et al., The Binding Affinity of Human IgG for its High Affinity Fc Receptor is Determined by Multiple Amino Acides in the CH2 Domain and Its Modulated by the Hinge Region, J. Exp. Med., 173:1483-1491 (1991).

Chalaris et al., Apoptosis is a natural stimulus of IL6R shedding and contributed to the proinflammatory trans-signaling function of neutrophils, Blood, 110(6):1748-1755 (2007).

Chow et al., A structural template for gp130-cytokine signaling assemblies, Biochimica et Biophasica Acta, 1592(3):225-235 (2002).

Chow et al., In vitro reconstruction of recognition and activation complexes between interleukin-6 and gp130, Biochemistry, 40(25):7593-7603 (2001).

Colbere-Garapin et al., A New Dominant Hybrid Selective Marker for Higher Eukaryotic Cells, J. Mol. Biol., 150:1-14 (1981).

Coruzzi et al., Tissue-specific and light-regulated expression of a pea nuclear gene encoding the small subunit of ribulose-1,5-bisphosphate carboxylase, The EMBO Journal, 3(8):1671-1679 (1984).

Cunningham et al., Receptor and antibody epitopes in human growth hormone identified by homolog-scanning mutagenesis, Science, 10(4896):1330-1336 (1989).

Cunningham et al., High-resolution epitope mapping of hGH-receptor interactions by alanine-scanning mutagenesis, Science 244(4908):1081-1085 (1989).

Darnell, Jr., STATs and Gene Regulation, Science, 277:1630-1635 (1997).

Deisenhofer, Crystallographic Refinement and Atomic Models of a Human Fc Fragment and Its Complex with Fragment B of Protein A from *Staphylococcus aureus* at 2.9- and 2.8-A Resolution, Biochem., 20(9):2361-2370 (1981).

Duncan et al., Localization of the binding site for the human high-affinity Fc receptor on IgG, Nature, 332:563-564 (1988).

Eck et al., Goodman & Gilmans the Pharmacological Basis of Therapeutics, Ninth Edition, McGraw-Hill, pp. 77-101 (1996).

Economides et al., Cytokine traps: multi-component, high-affinity blockers of cytokine action, Nature Medicine, 9(1):47-52 (2003).

Economides et al., Designer Cytokines: Targeting Actions to Cells of Choice, Science, 270:1351-1353 (1995).

Edwards et al., The Formation of a structure with the features of synovial lining by subcutaneous injection of air: an in vivo tissue culture system, J. Pathology, 134:147-156 (1981).

Engelhard et al., The insect tracheal system: A conduit for the systemic spread of Autographa califonica M nuclear polyhedrosis virus, Proc. Natl., Acad. Sci., 91:3224-3227 (1994).

Fingl et al., Goodman & Gilmans: The Pharmacological Basis for Therapeutics, Pharmacokinetics, Macmillan Publishing Co. NY, pp. 1-46 (1975).

Fingl et al., The Pharmacological Basis of Therapeutics, Goodman Gilman Eds. Macmilliam Publishing Co., pp. 1-46 (1975).

Fischer et al., A bioactive designer cytokine for human hematopoietic progenitor cell expansion, Nature Biotechnology, 15:142-145 (1997).

Friend et al., Phase I Study of an Engineered Aglycosylated Humanized CD3 Antibody in Renal Transplant Rejection, Transplantation, 68(11):1632-1637 (1999).

Fuglsang, Codon optimizer: a freeware tool for codon optimization, Protein Expr. Purif., 2:247-249 (2003).

Gao et al., UpGene: Application of Web-Based DNA Codon Optimization Algorithm, Biotechnol. Prog., 20:443-448 (2004).

Gellissen et al., New yeast expression platforms based on mehtylotrophic Hansenula polymorpha and *Pichia pastoris* and on dimorphic *Arxula adeninivorans* and *Yarrowia lipolytica*—A comparison, FEMS Yeast Research, 5:1079-1096 (2005).

Giese et al., Dimerization of the cytokine receptors gp130 and LIFR analysed in single cells, Journal of Cell Science, 118(21):5129-5140 (2005).

Gomord et al., Biopharmaceutical production in plants: problems, solutions and opportunities, TRENDS in Biotechnology, 23(11):559-561 (2005).

Goodson et al., Site-Directed Pegylation of Recombinant Interleukin-2 at Its Glygosylation Site, Biotechnology, 8:343-346 (1990).

Grace et al., Structural and Biologic Characterization of Pegylated Recombinant IFN-α2b, Jr. of Interferon and Cytokine Research, 21:1103-1115 (2001).

Greenhill et al., Il-6 Trans-Signaling Modulates TLR4-Dependent Inflammatory Responses via STAT3, J. of Immunology, 186:1199-1208 (2011).

Grotzinger et al., IL-6 Type Cytokine Receptor Complexes: Hexamer, Tetramer or Both?, Biol. Chem., 380:803-813 (1999).

Grotzinger et al., The Family of the IL-6-Type Cytokines: Specificity and Promiscuity of the Receptor Complexes, Proteins: Structure, Function and Genetics, 27:96-109 (1997).

Hartman et al., Two-dominant-acting selectable markers for gene transfer studies in mammalian cells, Proc. Natl. Acad. Sci., 85:8047-8051 (1988).

Herold et al., Anti-CD3 Monoclonal Antibody of New-Onset Type I Diabetes Mellitus, New England J. of Med., 346(22):1692-1698 (2002).

Hobbs et al., Genetic Engineering, McCraw Hill, New York, NY, pp. 191-196 (1992).

Horsten et al., The membrane distal half of gp130 is responsible for the formation of ternary complex with IL-6 and the IL-6 and receptor, FEBS Lett., 360(1):43-46 (1995).

Inoue et al., A highly enhanced thrombopoietic activity by monomethoxy polyethylene glycol-modified recombinant human interleukin-6, J. Lab. Clin. Med., 124(4):529-536 (1994).

Isaacs et al., Therapy with Monoclonal Antibodies. II The Contribution of Fcτ Receptor Binding and the Influence of CH1 and CH3 Domains on In Vivo Effector Function, J. of Immunology, 161:3862-3869 (1998).

JAVA, Codon Adaptation Tool—JCAT http://www.jcat.de retrieved Oct. 9, 2008.

Jefferis et al., IgG-Fc-medicated effector functions: molecular definition of interaction sites for effector ligands and the role of glycosylation, Immunological Review, 163:59-76 (1998).

Jefferis et al., Interaction sites on human IgG-Fc for FcγR: current models, Immunology Letters, 82:57-65 (2002).

Jefferis et al., Recognition sites on human IgG for Fcγ receptors: the role of flycosylation, Immunology Letters, 44:111-117 (1995).

Jones et al., Loss of CD4 T Cell IL-6R Expression during Inflammation Underlines a Role for IL-6 Trans-Signaling in the Local Maintenance of Th17 Cells, J. Immunol., 184:2130-2139 (2010).

Jostock et al., Immunoadhesins of interleukin-6 and the IL-6/soluble IL-6R fusion protein hyper-IL-6, Jr. of Immunological Methods, 223:171-183 (1999).

Jostock et al., Soluble gp130 is the nature inhibitor of soluble interleukin-6 receptor transsignaling responses, Eur. J. Biochem., 268:160-167 (2001).

Kallen, K.J., The role of transsignaling via the agonistic soluble IL-6 receptor in human diseases, Biochem. Biophys. Acta, 1592:323-343 (2002).

Katre, Immunogenicity of Recombinant IL-2 Modified by Covalent Attachment of Polyethylene Glycol., Jr. of Immunology, 144(1):209-213 (1990).

Kishimoto et al., Interleukin-6 Family of Cytokines and gp130, Blood, 86(4):1243-1254 (1995).

Kohler et al., Continuous cultures of fused cells secreting antibody of predefined specificity, Nature, 256:495-497 (1975).

Krapp et al., Structural Analysis of Human IgG-Fc Glycoforms Reveals Correlation Between Glycosylation and Structural Integrity, J. Mol. Biol., 325:979-989 (2003).

Krause et al., Rheumatoid arthritis synoviocyte survival is dependent on Stat3, J. Immunol., 169(11):6610-6616 (2002).

(56) References Cited

OTHER PUBLICATIONS

Lazar et al., Transforming Growth Factor α: Mutation of Aspartic Acid 47 and Leucine 48 Results in Different Biological Activities, Molecular & Cellular Biol., 8(3):1247-1252 (1988).
Levy et al., What does Stat3 do?, J. Clin. Invest., 109(9):1143-1148 (2002).
Lo et al., Il-6 Trans-Signaling in Formation and Progression of Malignant Ascites in Ovarian Cancer, Cancer Res., 71(2):424-434 (2011).
Logan et al., Adenovirus tripartite leader sequence enhances translation of mRNAS later after infection, Proc. Natl. Acad. Sci., 81(12):3655-3659 (1984).
Lowy et al., Isolation of Transforming DNA: Cloning the Hamster aprt Gene, Cell, 22:817-823 (1980).
Lowy et al., Isolation of Transforming DNA: Cloning the Hamster aprt Gene, Cell. 22:817-823 (1980).
MacAuley-Patrick et al., Heterologous protein production using the *Pichia pastoris* expression system, Yeast, 22:249-270 (2005).
Matsumiya et al., Structural Comparison of Fucosylated and Nonfucosylated Fc Fragments of Human Immunoglobulin G1, J. Mol. Biol., 368:767-779 (2007).
Matsumoto et al., Essential Roles of Il-6 Trans-Signaling in Colonic Epithelial Cells, Induced by the IL-6/Soluble-IL-6 Receptor Derived from Lamina Propria Macrophasees on Development of Colitis-Associated Premalignant Cancer in a Murine Model, J. of Immunol., 1544-1551 (2010.
Mikayama et al., Molecular cloning and functional expression of cDNA encoding glycosylation-inhibiting factor, Proc. Natl., Acad. Sci., 90:10056-10060 (1993).
Mitsuyama et al., STAT3 activation via interleukin 6 trans-signaling contributes to ileitis in SAMP1/Yit mice, Gut, 5:1263-1269 (2006).
Müllberg et al., IL-6 receptor independent stimulation of human gp130 by viral IL-6, J. Immunol., 164(9):4672-4677 (2000).
Murry, L.E., Agrobacterium-Mediated plant transformation in McGraw Hill Yearbook of Science and Technology, McGraw Hill, New York, pp. 191-196 (1992).
Nakamura et al., Codon usage tabulated from the international DNA sequence databases, Nucleic Acids Research, 24(1):214-215 (1996).
Nishimoto et al., Anticytokine therapy in autoimmune diseases, Intern. Med., 38(2):178-182 (1999).
Nishimoto, T., A new role of ran GTPase, Biochem. Biophys. Res. Commun., 262(3):571-574 (1999).
Nose et al., Biological significance of carbohydrates chains on monoclonal antibodies, Proc. Natl. Acad. Sci., 80:6632-6636 (1983).
Nowell et al., Therapeutic Targeting of IL-6 Trans-Signaling Counteracts STAT3 Control of Experimental Inflammatory Arthritis, J. of Immunology, 182:614-622 (2009).
Oganesyan et al., Structural characterization of mutated, ADCC-enhances human Fc fragment, Molecular Immunology, 45:1872-1882 (2008).
Oppmann et al., Alternative assay procedures for cytokines and soluble receptors of the IL-6 family, J. of Immunological Methods, 195:153-159 (1996).
Peipp et al., Molecular Engineering III: Fc Engineering, Handbook of Therapeutic Antibodies, pp. 171-196 (2007).
Pepinsky et al., Improved Pharmacokinetic Properties of Polyethylene Glycol-Modified Form of Interferon-β-1a with Preserved in Vitro Bioactivity, Jr. of Pharmacology and Experimental Therapeutics, 297(3):1059-1066 (2001).
Peters et al., In vivo and in vitro activities of the gp130-Stimulating Designer Cytokine Hyper-IL-6, J. of Immunology, 161:3575-3581 (1998).
Petit et al., Structure-Function Studies of Interleukin 15 using Site-specific Mutagenesis, Polyethylen Glycol Conjugation, and Homology Modeling, Jr. of Biological Chemistry, 272(4):2312-2318 (1997).
Rabe et al., Transgenic blockade of interleukin 6 transsignaling abrogates inflammation, Blood, 111:1021-1028 (2008).
Rakemann et al., The designer cytokine hyper-interleukin 6 is a potent activator of STAT3-dependent gene transcription in vivo and in vitro, J. Biol. Chem., 274(3):1257-1266 (1999).
Rhodes et al., Identification of MRF4; a new number of muscle regulatory factor gene family, Genes Dev., 3:2050-2061 (1989).
Rhodes et al., Transformation of Maize by Electroporation of Embryos, Methods of Molecular Biology, 55:121-131 (1995).
Rhodes et al., Transformation of Maize by Electroporation of Embryos, Methods in Molecular Biology, 55:121-131 (1995).
Rose-John et al., Studies on the structure and regulation of the human hepatic interleukin-6 receptor, Eur. J. Biochem., 190:79-83 (1990).
Sambrook et al., Molecular Cloning: A Laboratory Manual—2nd Edition, Cold Spring Harbor Laboratory Press, pp. I-XXXVIII (1989).
Scharf et al., Heat stress promoters and transcription factors, Results Probl. Cell Differ, 20:125-162 (1994).
Schutt et al., Supplemental Material—Transsignaling of Interleukin-6 Crucially Contributes to Atherosclerosis in Mice, Arterior cler Thromb. Biol., 32(2):1-26 (2011).
Schutt et al., Transsignaling of Interleukin-6 Crucially Contributes to Atherosclerosis in Mice, Arterior cler Thromb. Vasc. Biol., 32(2):281-290 (2011).
Siam et al., Choosing and using Schzosaccharomyces pombe plasmids, Methods, 33:189-198 (2004).
Sondermann et al., The 3.2-Å crystal structure of the human IgG1 Fc fragment-FcγRIII complex, Nature, 406:267-273 (2000).
Sprang et al., Cytokine structural taxonomy and mechanisms of receptor engagement, Current Opinion in Structural Biology, 3:815-827 (1993).
Stoger et al., Sowing the seeds of success: pharmaceutical proteins from plants, Current Opinion in Biotechnology, 16:167-173 (2005).
Suzuki et al., CIS3/SOCS3/SSI3 plays a negative regulatory role in STAT3 activation and intestinal inflammation, J. Exp. Med., 193(4):471-481 (2001).
Takamatsu et al., Expression of bacterial chloramphenicol acetyltransferase gene in tobacco plants mediated by TMV-RNA, The EMBO Journal, 6(2):307-311 (1987).
Tanaka et al., Cloning of novel soluble gp130 and detection of its neutralizing autoantibodies in rheumatoid arthritis, J. Chem. Invest., 106:137-144 (2000).
Tang et al., Studies on the PEGylation of Protein at a Specific Site: Sulfhydryl-PEGylation of 97Cys-IFN-gamma, Sheng Wu Hua Xue Yu Sheng Wu Wu Li Xue Bao (Shanghai), 28(3):312-215 (1996) (in Chinese with English abstract).
Tao et al., Studies of Aglycosylated Chimeric Mouse-Human IgG, J. of Immunology, 143(8):2595-2601 (1989).
Tenhumber et al., 152 Characterization of Mutants of the Soluble CP130 Protein in Terms of their binding affinity against the IL6/SIL6R Complex, Cytokine Abstracts, 39:42 (2007).
Tsunoda et al., Selective enhancement of thrombopoetic activity of PEGylated interleukin 6 by a simple procedure using a reversible aminoprotective reagent, BR. J. Haematol., 112:181-188 (2001).
Turkson et al., STAT proteins: novel molecular targets for cancer drug discovery, Oncogene, 19(56):6613-6626 (2000).
UnitProt Interleukin-6 receptor beta chain precursor. HIBI: Interleukin signal transducer, XP002322123 retrieved from EBI Database accession No. P40189 abstract, Feb. 1, 1995.
Utset et al., Modified Anti-CD3 Therapy in Psoriatic Arthritis: A Phase I/II Clinical Trial, J. Rheum., 29:1907-1913 (2002).
Voet et al., Biochemistry, John Wiley and Sons, Inc., pp. 126 and 228-234 (1990).
Vriend et al., What if: A molecular modeling and drug design program, J. Mol. Graphics, 8:52-56 (1990).
Wada et al., Codon usage tabulated from the GenBank genetic sequence data, Nucleic Acids Re., 18(Supplemental):2367-2411 (1990).
Waetzig et al., p38 Mitogen-Activated Protein Kinase is Activated and Linked to TNF-β Signaling in Inflammatory Bowel Disease, Jr. of Immunology, 168:5342-5351 (2002).
Wahl et al., Improved Radioimaging and Tumor Localization with Monoclonal F(ab')2, J. of Nuclear Medicine, 24:316-325 (1983).
Waldmann et al., Metabolism of Immunoglobulins, Progr. Allergy, 13:1-110 (1969).

(56) References Cited

OTHER PUBLICATIONS

Ward et al., Influence of Interleukins-6 (IL-6) Dimerization of Formation of the High Affinity Hexameric IL-6 Receptor Complex, J. of Bio. Chem., 271(33):20138-20144 (1996).

Wells et al., Perspectives in Biochemistry: Additivity of Mutational Effects in Proteins, Biochem., 29(37):8509-8517 (1990).

Wigler et al., Transfer of Purified Herpes Virus Thymidine Kinase Gene to Cultured Mouse Cells, Cell 11:223-232 (1977).

Wigler et al., Transformation of mammalian cells with an amplifiable dominant-acting gene, Proc. Natl. Acad. Sci., 77(6):3567-3570 (1980).

Wildt et al., The Humanization of N-Glycosylation Pathways in Yeast, Nature Reviews, 3:119-128 (2005).

Wines et al., The IgG Fc Contains Distinc Fc Receptor (FcR) Binding Sites: The Leukocyte Receptors FcγRIIIa Bind to a Region in the Fc Distinct from that Recognized by Neonatal FcR and Protein A1, Jr. of Immunology, 164:5313-5318 (2000).

Winter et al., The Expression of Heat Shock Protein and Cognate Genes During Plant Development, Results and Problems in Cell Differentiation, pp. 85-105 (1991).

Woodle et al., Phase I Trial of Humanized, Fc Receptor nonbinding OKT3 Antibody huOKT3γ1(Ala-Ala) in the treatment of acute renal allograft rejection, Transplantation, 68(5):608-616 (1999).

Wright et al., Effect of glycosylation on antibody function: implications for genetic engineering, TibTech., 15:28-32 (1997).

Yoshizaki et al., Interleukin-6 in autoimmune disorders, Semin. Immunol., 4:155-166 (1992).

Youngster et al., Structure Biology and Therapeutic Implications of Pegylated Interferon Alpha-2b, Current Pharmaceutical Design, 8:2139-2157 (2002).

Mitsuyama, K. et al., Therapeutic Strategies for Targeting the IL-6/STAT3 Cytokine Signaling Pathway in Inflammatory Bowel Disease, Anticancer Research, 27: 3749-3756 (2007).

Rose-John, S. et al., The IL-6/sIL-6R complex as a novel target for the therapeutic approaches, Expert Opin. Ther. Targets, 11(5): 613-624 (2007).

SGP130/FC DIMERS FOR TREATMENT OF INFLAMMATORY DISEASE

This application is a divisional of U.S. application Ser. No. 12/307,003, filed Dec. 30, 2008, which was the National Stage of International Application No. PCT/EP2007/005812, filed Jun. 29, 2007, which claims the benefit of European Application No. 06013668.6, filed Jun. 30, 2006, the entire contents of each of which are hereby incorporated by reference herein.

The present invention relates to a polypeptide dimer comprising two soluble gp130 molecules each being fused to an Fc domain of an IgG1 protein wherein the hinge region of the Fc domain is modified resulting in advantageous properties of the dimer. The present invention also relates to a pharmaceutical composition containing said dimer and various medical uses.

The pleiotropic cytokine interleukin-6 (IL-6) shows a wide spectrum of biological functions among which stimulation of B cells and induction of acute phase protein synthesis in liver are mostly notable. IL-6 exerts its activity on target cells via binding to an IL-6 specific surface receptor (IL-6R). This receptor/ligand complex facilitates homodimerization of gp130, the second subunit of the IL-6 receptor complex. Dimerization of gp130 results in transduction of an IL-6 signal. Soluble forms of the IL-6R (sIL-6R) which are generated by two mechanisms (alternative splicing and shedding) are also able to trigger gp130 dimerization and signalling when complexed with IL-6.

Since the cytoplasmic portion of the IL-6R does not contribute to signal transduction, signalling by a gp130 homodimer can be induced by IL-6 in complex with membrane bound or soluble IL-6R. The presence of sIL-6R, however, leads to sensitization of IL-6 responsive cells towards the ligand. Furthermore, strictly IL-6 dependent hybridoma cells do not proliferate in response to very low amounts of IL-6 when sIL-6R present in culture media is continuously removed.

Initially described as the interleukin-6 signal transducer, gp130 is a transducer chain shared by many cytokines, such as IL-6, IL-11, leukaemia inhibitory factor (LIF), oncostatin M (OSM) and ciliary neurotrophic factor (CNTF). All of these cytokines act via a bi- or tripartite receptor complex in which signalling is triggered by homodimerization (for IL-6) or heterodimerization of gp130 with LIF-R (for LIF, CT-1, OSM, CLC and CNTF) or OSM-R (for OSM). These cytokines can thus mediate similar biologic activities in various tissues.

While gp130 can be found on nearly all cell types, the IL-6R shows a much more restricted expression. The release of sIL-6R by one cell type renders other cells, which only express gp130, responsive to IL-6. This scenario is called trans-signalling. Indeed, several cellular activities have been described which require the complex of sIL-6R and IL-6 and are not seen with IL-6 alone. Soluble gp130 protein is found in high concentrations in human plasma. Recently the designer-cytokine hyper-LL-6 (H-IL-6), in which the C-terminus of sIL-6R is covalently fused to the N-terminus of mature IL-6 by a flexible peptide linker, has been described. As seen with the complex of IL-6/sIL-6R, H-IL-6 also acts on cells which only express gp130. In contrast to the separate components IL-6 and sIL-6R, a 100 to 1000 fold lower concentration of this fusion molecule is sufficient to induce comparable biological signals.

For the treatment of various diseases or disorders, specific blocking of IL-6 responses dependent on soluble IL-6R might be desirable. Such diseases include bone resorption, hypercalcemia, cachexia, tumors or other types of cancer (e.g., colon cancer, multiple myeloma, lymphoma, leukaemia, Hodgkin's disease), autoimmune diseases (e.g., multiple sclerosis (MS) or type 1 diabetes), inflammatory or atopic diseases (e.g., Crohn's disease, ulcerative colitis, rheumatoid arthritis, juvenile rheumatoid arthritis, asthma, psoriasis, sarcoidosis, lupus erythematosus or uveitis), infections (e.g., by bacteria, viruses, fungi, or other pathogens), as well as endocrinologic disorders and metabolic or catabolic diseases (e.g., type 2 diabetes, obesity, hyperglycemia or hypercholesterinemia). It was found that, e.g., sgp130 dimers or sgp130Fc dimers are useful for therapeutic applications.

The technical problem underlying the present invention was to provide improved sgp130Fc dimers.

The solution of said technical problem is achieved by providing the embodiments characterized in the claims. During the experiments leading to the present invention it was found that the biological activity, purifiability and stability of sgp130Fc fusion proteins significantly depends on the amino acid composition of the hinge region between the sgp130 and the Fc part. The amino acids 234, 235 and 237 of the human IgG1-Fc (according to EU numbering) were mutated in order to reduce Fc receptor binding to this motif (Duncan et al., Nature (1988), 332: 563-564; Canfield and Morrison, J. Exp. Med. (1991), 173: 1483-1491; Wines et al., J. Immunol. (2000), 164: 5313-5318; Sondermann et al., Nature (2000), 406: 267). Unexpectedly, by replacing $Leu_{235}$ of the wild type sequence $Leu_{234}$-$Leu_{235}$-$Gly_{236}$-$Gly_{237}$ with glutamate (Glu, E) or aspartate (Asp, D) and, thus, breaking the hydrophobic motif with a strongly hydrophilic (charged) amino acid the biological activity and stability of sgp130Fc fusion proteins could be improved. Mutations in position 234 and 237 add to this effect. The most potent mutant features the sequence $Ala_{234}$-$Glu_{235}$-$Gly_{236}$-$Ala_{237}$.

The lower hinge region of human IgG1-Fc was modified by site-directed mutagenesis. The ideal sequence, as determined in the experiments, is "AEGA" (as incorporated in the compound CR5/18).

Abbreviations and symbols: aa, amino acid(s); C, cysteines forming the two disulfide bridges needed for dimerization of the Fc fusion protein; X, alanine (Ala, A) or phenylalanine (Phe, F); Z, glutamate (Glu, E) or Aspartate (Asp, D).

Figure 1:
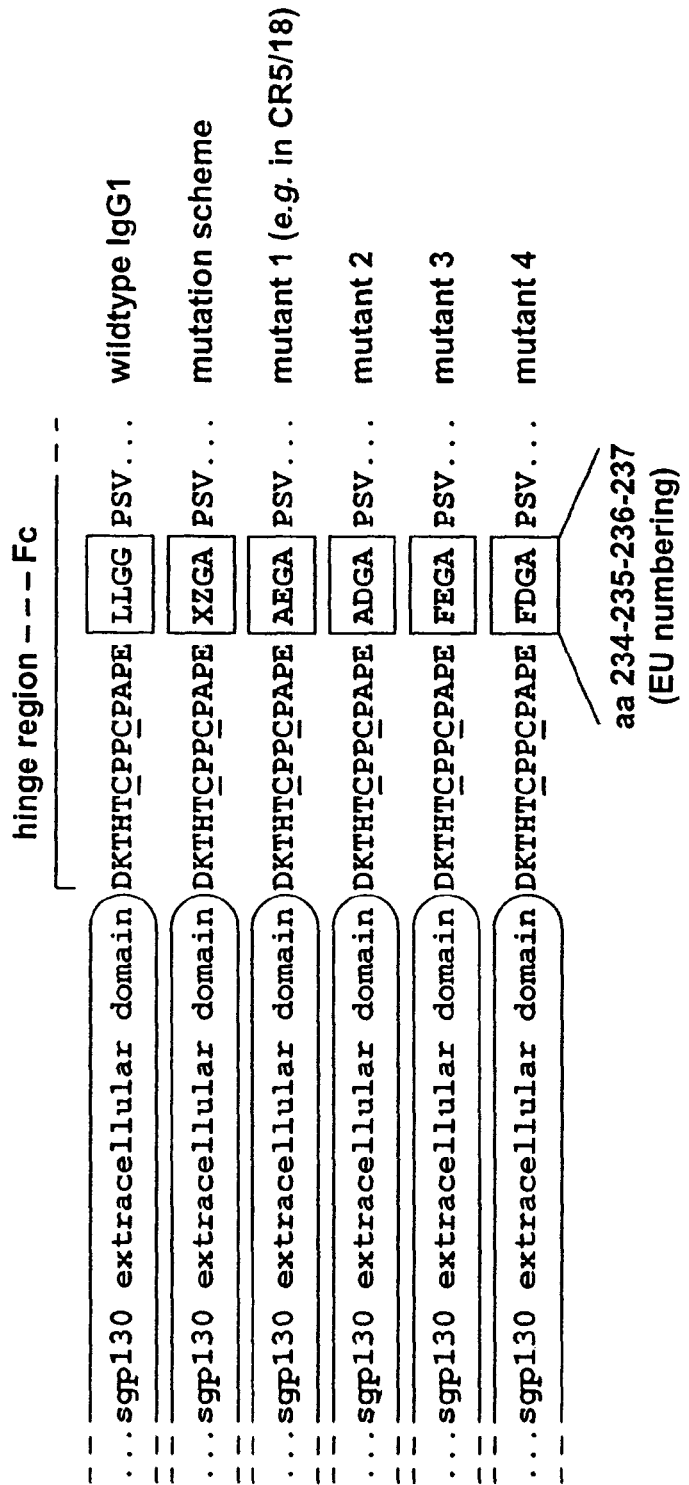
FIG. 1: Hinge region muteins of sgp130Fc
Figure 2:
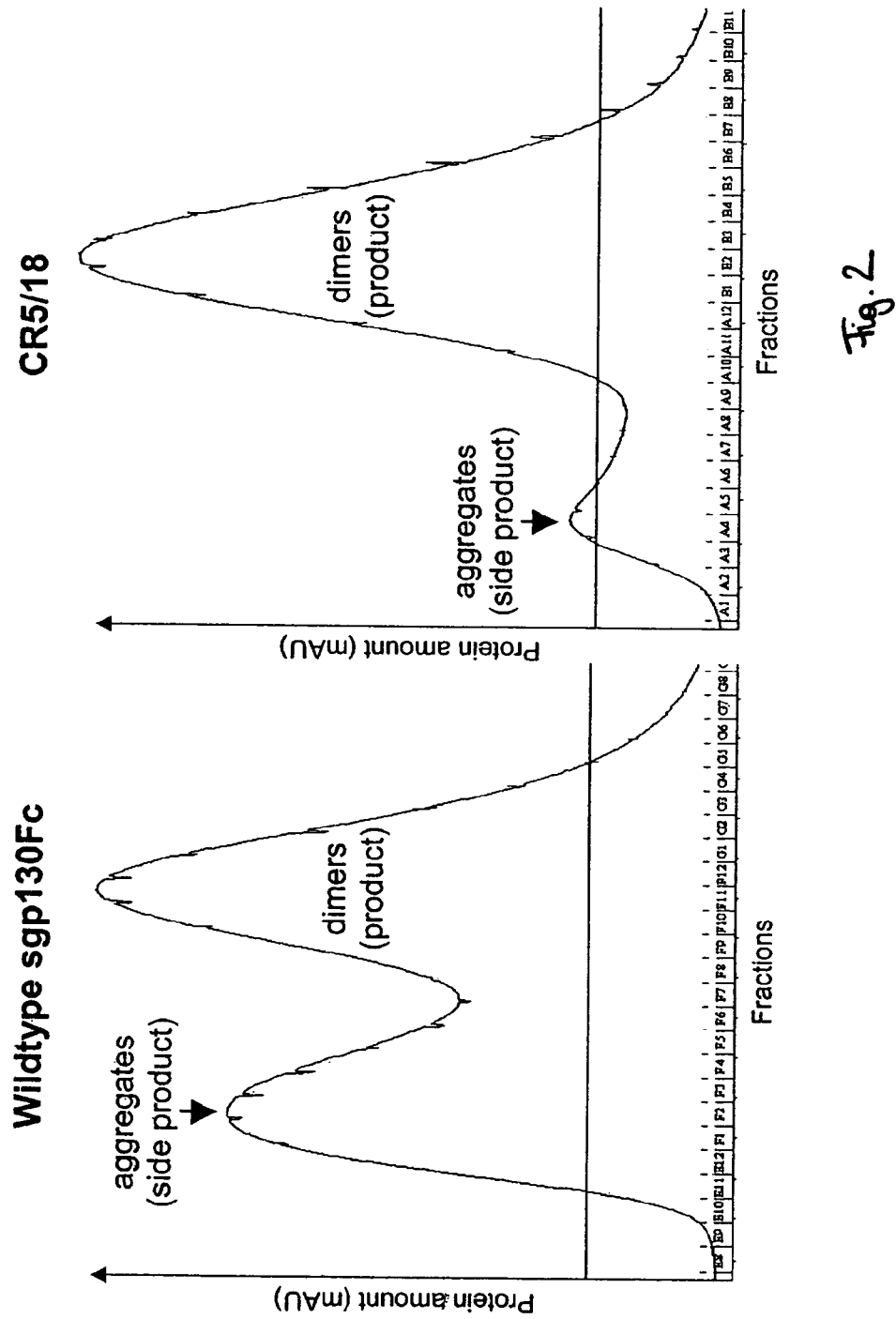

FIG. 2: Size exclusion chromatography elution curves of wildtype sgp130Fc and CR5/18

CR5/18 shows a significantly reduced amount of aggregates (side products) compared to wild type sgp130Fc and, thus, a higher yield of uncontaminated product.

Figure 3:
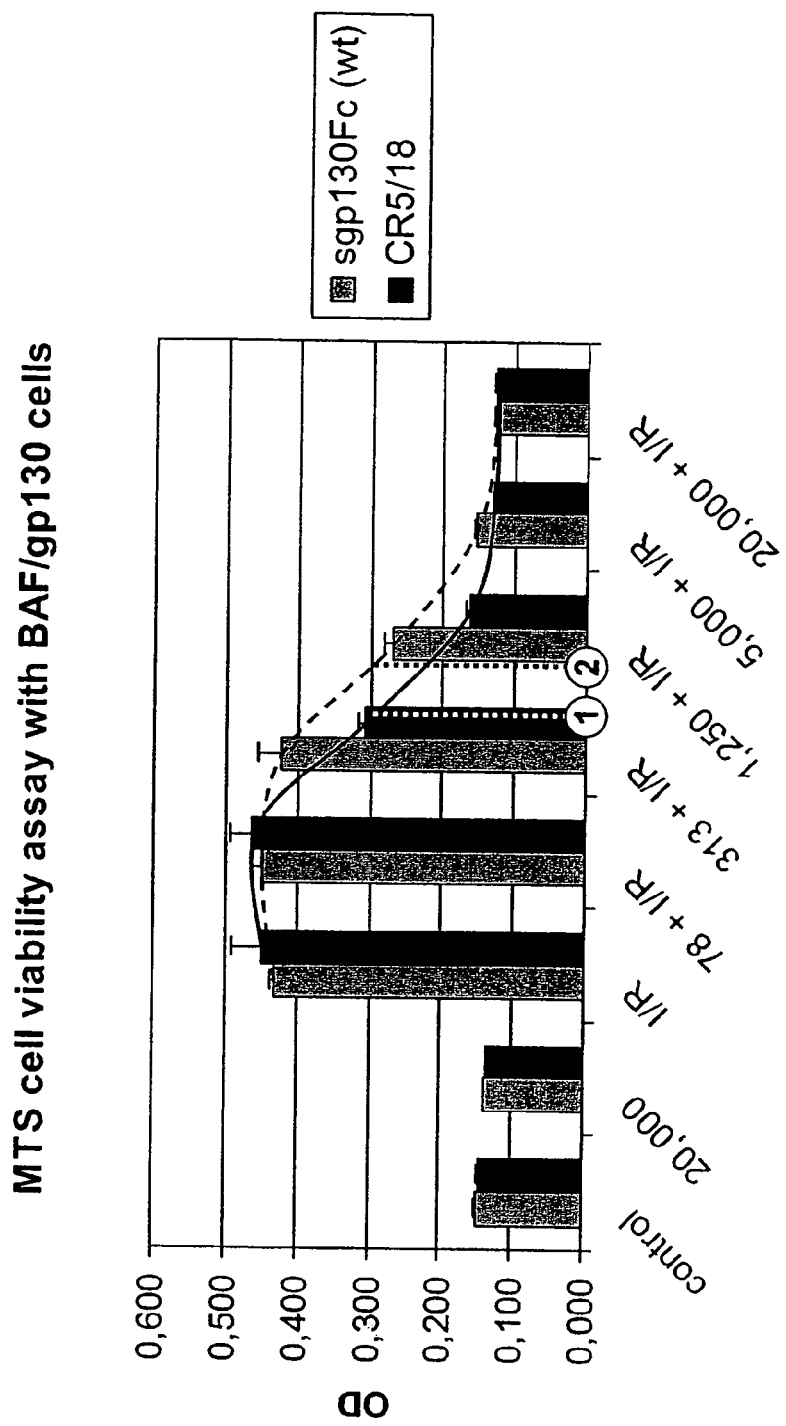

FIG. 3: Inhibition of IL-6/sIL-6R-induced proliferation of BAF3/gp130 cells by CR5/18 or wildtype sgp130Fc as determined by MTS cell viability assays CR5/18 is significantly more biologically active than wild type (wt) sgp130Fc in blocking proliferation triggered by 100 ng/mL IL-6 and 50 ng/mL sIL-6R. This is reflected by the $IC_{50}$ of CR5/18 (1), which is about half the $IC_{50}$ of sgp130Fc (2). Abbreviations and symbols: $IC_{50}$, concentration with 50% inhibitory efficacy; IL-6, interleukin-6; I/R, IL-6 plus sIL-6R; MTS, substrate which is converted by metabolically active cells to a soluble formazan product absorbing at 490 nm; OD, optical density at 490 nm; sIL-6R, soluble interleukin-6 receptor.

Thus, the present invention relates to a polypeptide-dimer capable of inhibiting the activity of the agonistic complex IL-6/sIL-6R and comprising two monomers wherein each monomer comprises a soluble gp130 molecule or variant or fragment thereof fused to an Fc domain of an IgG protein and wherein at least the amino acid residue $Leu_{235}$ of the hinge region of the Fc domain is replaced by at least one hydrophilic amino acid residue. Preferred hydrophilic amino acid residues are Glu and Asp.

The term "soluble" as used herein refers to a gp130 molecule lacking the intracellular domain and, preferably, the transmembrane domain.

The dimers of the present invention may be engineered using known methods. The domains utilized may consist of the entire extracellular domain of gp130 or they may consist of mutants or fragments thereof that maintain the ability to inhibit the activity of the agonistic complex IL-6/sIL-6R. Preferred fragments are fragments consisting at least of the extracellular domains D1 to D3.

The expression "fused to an Fc domain of an IgG protein" means that, preferably, the fusion partner of the dimer merely consists of the Fc domain of the IgG1 protein. However, the Fc part may comprise sequences from more than one IgG isotype, and selecting particular sequence motifs to optimize desired effector functions is within the ordinary skill in the art.

In a preferred embodiment of the polypeptide dimer of the present invention, the hinge region amino acid residue $Leu_{234}$ is replaced by Phe or Ala.

In a more preferred embodiment of the polypeptide dimer of the present invention, the amino acid residues $Leu_{234}$ and/or $Gly_{237}$ of the hinge region are replaced by the amino acid residue Ala.

In an even more preferred embodiment of the polypeptide dimer of the present invention, the hinge region comprises the amino acid sequence motif $Ala_{234}$-$Glu_{235}$-$Gly236$-$Ala_{237}$ instead of $Leu_{234}$-$Leu_{235}$-$Gly_{236}$-$Gly_{237}$.

Particularly preferred is a polypeptide dimer, wherein the hinge region comprises the amino acid sequence $Asp_{221}$-$Lys_{222}$-$Thr_{223}$-$His_{224}$-$Thr_{225}$-$Cys_{226}$-$Pro_{227}$-$Pro_{228}$-$Cyx_{229}$-$Pro_{230}$-$Ala_{231}$-$Pro_{232}$-$Glu_{233}$-$Ala_{234}$-$Glu_{235}$-$Gly_{236}$-$Ala_{237}$-$Pro_{238}$-$Ser_{239}$-$Val_{240}$.

The fusions of the gp130 extracellular domain (sgp130), preferably at the C-terminus, or the variant or fragment thereof to the hinge region of the Fc part may be direct or they may employ a flexible polypeptide linker domain of various lengths and amino acid combinations. These linkers may be entirely artificial (e.g., comprising 2-50 amino acid residues independently selected from the group consisting of glycine, serine, asparagine, threonine and alanine) or adopted from naturally occurring proteins. Such linkers can enhance flexibility and binding properties of the dimer.

Additionally, the sgp130Fc fusion proteins of the invention may be further fused to tags, such as poly(His), Myc, Strep, polyarginine, Flag, green fluorescent protein (GFP), TAP, glutathione S-transferase (GST), HA, calmodulin-binding peptide (CBP), maltose-binding protein (MBP), V5, HSV, S, vesicular stomatitis virus (VSV), Protein C, Luciferase, Glu-Glu, E, beta-GAL, T7 or other epitopes to which antibodies or other binding molecules are available to allow rapid purification, detection in Western blot or ELISA, immunoprecipitation, or activity depletion/blocking in bioassays.

In a further preferred embodiment of the polypeptide dimer of the present invention, one or more N-glycosylation sites are inserted between the soluble gp130 molecule or variant or fragment and the Fc domain. Amino acid motifs of N-glycosylation sites with the core sequence Asn-X-Ser or Asn-X-Thr depend on the context of the motif in the protein and can be predicted and designed by the person skilled in the art, e.g. by using free software such as NetNGlyc (Center for Biological Sequence Analysis, Technical University of Denmark). A preferred N-glycosylation linker element for sgp130Fc dimers of the invention is His-Asn-Leu-Ser-Val-Ile.

Another object of the present invention are PEGylated or other chemically modified forms of the dimers. PEGylation of the sgp130 molecules can be carried out, e.g., according to the methods described for human IFN-γ, IFN-α, IFN-β, IL-15 or IL-2 (Youngster et al., Curr Pharm Des (2002), 8:2139; Grace et al., J Interferon Cytokine Res (2001), 21:1103; Pepinsky et al., J Pharmacol Exp Ther (2001), 297:1059; Pettit et al., J Biol Chem (1997), 272:2312; Goodson et al. Biotechnology NY (1990), 8:343; Katre; J Immunol (1990), 144: 209).

Any kind of polyethylene glycol is suitable for the present invention provided that the PEG-polypeptide-dimer is still capable of blocking IL-6 responses dependent on sIL-6R which can be assayed according to methods known in the art.

Preferably, the polyethylene glycol of the polypeptide-dimer of the present invention is PEG 1000, 2000, 3000, 5000, 10000, 15000, 20000 or 40000 with PEG 20000 or 40000 being particularly preferred.

In order to form the dimer the two soluble gp130 molecules are linked to each other through a simple covalent bond, a flexible peptide linker or, preferably, via one or more disulfide bridges. Peptide linkers may be entirely artificial (e.g., comprising 2 to 20 amino acid residues independently selected from the group consisting of glycine, serine, asparagine, threonine and alanine) or adopted from naturally occurring proteins. Disulfide bridge formation can be achieved, e.g., by recombinant expression, wherein the nucleic acid sequence encoding the sgp130Fc monomer contains one or more cysteine encoding codons, preferably in the hinge region of the Fc domain.

The dimers of the present invention are preferably recombinantly produced by use of a polynucleotide encoding a monomer of the dimer and vectors, preferably expression vectors containing said polynucleotides. For the production of the dimers of the invention, the polynucleotides are obtained from existing clones, i.e., preferably encode the naturally occurring polypeptide or a part thereof (for human gp130/IL6ST: GenBank sequence NM_002184 and supporting clones; for the constant region of human IgG1/IGHG1: e.g., GenBank sequence AK057754). Polypeptides encoded by any polynucleotide which hybridises to the complement of the native DNA or RNA under highly stringent or moderate stringent conditions (for definitions, see Sambrook, Molecular Cloning A Laboratory Manual, Cold Spring Harbor Laboratory (1989) N.Y.) as long as that polypeptide maintains the biological activity of the native sequence, are also useful for producing the dimers of the present invention.

The recombinant vectors can be constructed according to methods well known to the person skilled in the art; see, e.g., Sambrook, Molecular Cloning A Laboratory Manual, Cold Spring Harbor Laboratory (1989) N.Y. A variety of expression vector/host systems may be utilised to contain and express sequences encoding the dimers of the present invention. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

In bacterial systems, a number of expression vectors may be selected depending upon the use intended for the polypeptide dimer of the present invention. Vectors suitable for use in the present invention include, but are not limited to the pSKK expression vector for expression in bacteria.

In wild type or modified (e.g., glycoengineered) yeast species, such as *Saccharomyces cerevisiae, Schizosaccharomyces pombe* or *Pichia pastoris*, a number of vectors containing constitutive or inducible promoters or promoter systems such as alpha factor, alcohol oxidase, PGH, tetracycline glucose etc. may be used; for reviews, see Grant et al. (1987) Methods Enzymol. 153:516-544; Siam et al. (2004) Methods 33:189-198; Macauley-Patrick et al. (2005) Yeast 22:249-270, Gellissen et al. (2005) FEMS Yeast Res. 5:1079-1096; Wildt and Gerngross (2005) Nat. Rev. Microbiol. 3:119-128.

In cases where state of the art plant expression systems are used (for review, see, e.g., Stoger et al. (2005) Curr. Opin. Biotechnol. 16:167-173; Gomord et al. (2005) Trends Biotechnol. 23:559-565) the expression of sequences encoding a dimer (or monomers thereof) of the present invention may be driven by any of a number of promoters. For example, viral promoters such as the 35S and 19S promoters of CaMV may be used alone or in combination with the omega leader sequence from TMV (Takamatsu (1987) EMBO J. 6:307-311). Alternatively, plant promoters such as the small subunit of RUBISCO or heat shock promoters may be used (Coruzzi et al. (1984) EMBO J. 3:1671-1680; Broglie et al. (1984) Science 224:838-843; and Winter et al. (1991) Results Probl. Cell Differ. 17:85-105). These constructs can be introduced into plant cells by direct DNA transformation or pathogen-mediated transfection. Such techniques are described in a number of generally available reviews (see, for example, Hobbs and Murry in McGraw Hill Yearbook of Science and Technology (1992) McGraw Hill, N.Y., pp. 191-196).

An insect system may also be used to express the dimers (or the monomers thereof) of the present invention. For example, in one such system, *Autographs californica* nuclear polyhedrosis virus (AcNPV) is used as a vector to express foreign genes in *Spodoptera frugiperda* cells or in *Trichoplusia larvae*. The sequences may be cloned into a non-essential region of the virus, such as the polyhedrin gene, and placed under control of the polyhedrin promoter. Successful insertion of the DNA sequence encoding sgp130Fc monomers or fragments or variants thereof will render the polyhedrin gene inactive and produce recombinant virus lacking coat protein. The recombinant viruses may then be used to infect, for example, *S. frugiperda* cells or *Trichoplusia larvae* in which sgp130Fc of the present invention may be expressed (Engelhard et al. (1994) Proc. Nat. Acad. Sci. 91:3224-3227).

In mammalian host cells, a number of expression systems based, e.g., on lipid-based transfection or viral transduction of the cells may be utilised. In cases where an adenovirus is used as an expression vector, sequences encoding the polypeptide(s) of the present invention may be ligated into an adenovirus transcription/translation complex consisting of the late promoter and tripartite leader sequence. Insertion in a non-essential E1 or E3 region of the viral genome may be used to obtain a viable virus which is capable of expressing the polypeptides of the present invention in infected host cells (Logan, J. and Shenk, T. (1984) Proc. Natl. Acad. Sci. 81:3655-3659). In addition, transcription enhancers, such as the Rous sarcoma virus (RSV) enhancer, may be used to increase expression in mammalian host cells.

After the introduction of the recombinant vector(s), the host cells are grown in a selective medium, which selects for the growth of vector-containing cells. Any number of selection systems may be used to recover transformed cell lines. These include, but are not limited to, the herpes simplex virus thymidine kinase (Wigler, M. et al. (1977) Cell 11:223-32) and adenine phosphoribosyltransferase (Lowy, I. et al. (1980) Cell 22:817-23) genes which can be employed in tk.sup.− or aprt.sup.− cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567-70); npt, which confers resistance to the aminoglycosides neomycin and G-418 (Colbere-Garapin, F. et al (1981) J. Mol. Biol. 150:1-14) and als or pat, which confer resistance to chlorsulfuron and phosphinotricin acetyltransferase, respectively. Additional selectable genes have been described, for example, trpB, which allows cells to utilise indole in place of tryptophan, or hisD, which allows cells to utilise histinol in place of histidine (Hartman, S. C. and R. C. Mulligan (1988) Proc. Natl. Acad. Sci. 85:8047-51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121-131).

Purification of the recombinant polypeptides is carried out by any one of the methods known for this purpose, i.e., any conventional procedure involving extraction, precipitation, chromatography, electrophoresis, or the like. A further purification procedure that may be used is affinity chromatography using, e.g., Protein A, Protein G or monoclonal antibodies, which bind the target polypeptide and which are produced and immobilized on a gel matrix contained within a column. Impure preparations containing the recombinant polypeptide are passed through the column. The polypeptide will be bound to the column by the specific interaction with the affinity gel matrix while the impurities will pass through. After washing the polypeptide is eluted from the gel by a change in pH or ionic strength and then, if it is produced as the monomer, dimerized and, if desired, PEGylated.

Accordingly, the present invention also relates to a method of producing the polypeptide dimer of the present invention, comprising culturing a host cell transformed with a DNA sequence encoding a monomer of said polypeptide and recovering the polypeptide-monomer or dimer from said host cell or the culture.

The polypeptide dimers of the present invention are useful in the treatment and/or prevention of all the pathologies, in which the activity of the agonistic complex IL-6/sIL6R should be inhibited.

Thus, the present invention also relates to a pharmaceutical composition containing an effective amount of a polypeptide-dimer of the present invention, preferably combined with a pharmaceutically acceptable carrier. "Pharmaceutically acceptable" is meant to encompass any carrier, which does not interfere with the effectiveness of the biological activity of the active ingredient and that is not toxic to the host to which it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at an effective dose.

An "effective amount" refers to an amount of the active ingredient that is sufficient to affect the course and the severity of the disease, leading to the reduction or remission of such pathology.

An "effective dose" useful for treating and/or preventing these diseases or disorders may be determined using methods known to one skilled in the art (see for example, Fingl et al., The Pharmacological Basis of Therapeutics, Goodman and Gilman, eds. Macmillan Publishing Co., New York, pp. 1-46 ((1975)).

Administration of the compositions may be effected by different ways, e.g. by intravenous, intraperitoneal, subcutaneous, intramuscular, topical or intradermal administration. The dosage regimen will be determined by the attending physician and other clinical factors. As is well known in the medical arts, dosages for any one patient depend on many factors, including the patient's size, body surface area, age, sex, the particular compound to be administered, time and route of administration, the kind of therapy, general health and other drugs being administered concurrently.

The present invention also relates to the use of a polypeptide dimer as defined above for the preparation of a pharmaceutical composition for the treatment and/or prevention of a disease or disorder where blockage of the agonistic complex IL-6/sIL-6R has a beneficial effect. Preferred medical uses of the polypeptide-dimers of the present invention are the treatment/prevention of bone resorption, hypercalcemia, cachexia, tumors or other types of cancer (e.g., colon cancer, multiple myeloma, lymphoma, leukaemia or Hodgkin's disease), autoimmune diseases (e.g., multiple sclerosis or type 1 diabetes), inflammatory or atopic diseases (e.g., Crohn's disease, ulcerative colitis, rheumatoid arthritis, juvenile rheumatoid arthritis, asthma, psoriasis, sarcoidosis, lupus erythematosus or uveitis), infections (e.g., by bacteria, viruses, fungi or other pathogens), as well as endocrinologic disorders and metabolic or catabolic diseases (e.g., type 2 diabetes, obesity, hyperglycemia or hypercholesterinemia).

The examples below explain the invention in more detail.

EXAMPLE 1

Construction and Production of the sgp130Fc Mutein CR5/18

(A) Material

The Gateway cloning system components (AccuPrime Pfx DNA Polymerase, the donor vector pDONR221, the CMV promoter-controlled expression vector pcDNA-DEST40, BP and LR recombinase for insert transfer and competent *E. coli* cells) were purchased from Invitrogen (Karlsruhe, Germany). The QuikChange II site-directed mutagenesis kit was obtained from Stratagene (Amsterdam, The Netherlands). PAGE purified mutagenesis primers were from Microsynth (Balgach, Switzerland). CHO-K1 cells were obtained from the German Collection of Microorganisms and Cell Cultures (Braunschweig, Germany). Culture medium components were purchased as follows: Ham's F12 medium, low IgG FBS and PBS (PAA Laboratories; Cölbe, Germany), FBS (Biochrom; Berlin, Germany), Trypsin/EDTA solution (Invitrogen) and G418 solution (Sigma-Aldrich; Taufkirchen, Germany). The transfection reagent Lipofectamine 2000 was from Invitrogen. Santa Cruz (Heidelberg, Germany) supplied Protein A/G Plus Agarose for immunoprecipitation. For both immunoprecipitation and primary detection in Western blots, a mouse anti-human IgG (Fc) monoclonal antibody was used (CBL102; Chemicon; Hofheim, Germany). Western blot secondary detection was performed with an anti-mouse IgG HRP-linked antibody, ECL-Plus Western blotting substrate and Hyperfilm ECL (all from GE Healthcare; Munich, Germany).

Roller bottles (2.1 L, 2,5× surface) were purchased from Greiner Bio-One (Frickenhausen, Germany). Cellulose acetate filters (0.45 µm) for a vacuum filter unit were purchased from Sartorius (Göttingen, Germany). Materials for affinity and size exclusion chromatography (SEC) were all obtained from GE Healthcare (Munich, Germany): MabSelect material (product code 17-5199-01) in a XK16/20 column, PD-10 desalting columns and a HiLoad 26/60 Superdex 200 pg column for SEC. Amicon Ultra-15 50 kDa Ultracel-PL membrane concentration units were purchased from Millipore (Eschborn, Germany). Ready-made acrylamide-bis solution (19:1, 30%) for PAGE was supplied by Bio-Rad (Munich, Germany).

(B) Construction of CR5/18

A cDNA for full-length sgp130Fc comprising the complete extracellular domain of gp130 and the wildtype human IgG1 Fc (sources: for human gp130/IL6ST: GenBank sequence NM_002184 and supporting clones; for the constant region of human IgG1/IGHG1: e.g., GenBank sequence AK057754) was codon-optimized for expression in CHO-K1 cells and subcloned into pDONR221 using Gateway primers, AccuPrime Pfx DNA Polymerase and BP recombinase in a standard Gateway cloning procedure. The subcloned insert was completely sequence-verified using stacked forward and reverse sequencing primers every 250-300 bp. In a site-directed mutagenesis with the QuikChange II kit, the lower hinge region of the IgG1-Fc (amino acids 234, 235 and 237 according to EU numbering) were mutated from the wildtype sequence "LLGG" to "AEGA". Mutated clones were verified by complete sequencing as described above. Subsequently, the insert was transferred to the expression vector pcDNA-DEST40 by Gateway LR recombination. As the insert encodes two stop codons after the Fc part, the tags coded in pcDNA-DEST40 (V5 and 6× His epitopes) are not present in CR5/18. Positive clones were identified by AlwNI restriction digest and sequence verified again.

(C) Cell Culture and Transfection

CHO-K1 cells were grown in Ham's F12 medium supplemented with 10% FBS at 37° C. and 5% $CO_2$ in a water-saturated atmosphere. Maintenance cultures were split every 3-4 days and used only up to 20 passages. Cells were transfected with the expression construct pcDNA-DEST40_CR5/18 using Lipofectamine 2000 and standard conditions for CHO-K1 supplied by Invitrogen. For a first transient expression test, CHO-K1 cells were transfected in 6-well plates, and both, cells and supernatants, were harvested 24 h after transfection. CR5/18 was immunoprecipitated from the supernatants using Protein A/G Plus Agarose and the anti-human IgG (Fc) antibody according to the manufacturer's instructions. Whole cell protein was extracted and Western blots with anti-human IgG (Fc) antibody were performed with the cell lysates and immunoprecipitates as described in Waetzig et al., J. Immunol. 168: 5342 (2002).

(D) Production of CR5/18 in CHO-K1 Cells

After successful transient expression, CHO-K1 cells were transfected and positive clones were selected using 400 µg/ml G418 in 10 cm plates. To determine product quality and properties, a pre-selected polyclonal CHO-K1 pool was transferred to roller bottles and cultured with low IgG FBS. Supernatants of the confluent cells were harvested 2-3 times a week, centrifuged twice at 3,500×g and 4° C. for 15 min to remove cell debris and either processed immediately or frozen at −80° C. In parallel, stable cell clones were selected from the pre-selected pool using a limited dilution method and characterized by Western blot expression analysis as described above. The clone with the highest and most stable expression was transferred to roller bottles and used for permanent production.

(E) Purification by Affinity and Size Exclusion Chromatography

CR5/18-containing supernatants from roller bottle cultures were purified at 4° C. using a P-1 peristaltic pump and an ÄKTA Purifier 100 System (both from GE Healthcare; Munich, Germany). The protocol was based on the manufacturer's recommendations for the purification of monoclonal antibodies. After centrifugation, the pH of the fresh or thawed (on ice) supernatant was adjusted to 6.7-7.0. After two rounds of vacuum filtration (0.45 μm) the supernatant was degassed and—if necessary—the pH was adjusted again to a value of 6.7-7.0. Subsequently, the PBS-equilibrated affinity chromatography column (6-25 ml MabSelect in a XK16/20 column) was loaded with 2-4 L of supernatant at a flow rate of 3-10 ml/min using the P-1 pump. After washing with PBS, the column was transferred to the ÄKTA purifier and washed again with PBS until the $A_{280}$ stabilized after quantitative removal of unbound protein. For the elution, the ÄKTA system was equipped with two 50 mM sodium citrate buffers at pH 3.25 and 5.5, respectively, which were mixed to produce the desired pH conditions. One washing step at pH 5.1 was followed by elution with pH 3.7. Fractions of 10 ml were collected in 15 ml tubes containing 2 ml of 1 M Tris-HCl (pH 11). The peak fractions were pooled, and the pH was measured and adjusted to 7.5, if necessary. Pool protein concentration was measured by $A_{280}$ and the pool was carefully concentrated to a maximum of 1.5 mg/ml using Amicon Ultra-15 50 kDa Ultracel-PL membrane concentration units. PBS-equilibrated PD-10 desalting columns were used to replace the citrate buffer with PBS, followed by another protein concentration measurement at 280 nm.

For size exclusion chromatography (SEC), a maximum protein concentration of 1.2 mg/ml in PBS was recommendable. SEC was performed with the ÄKTA system in a PBS-equilibrated HiLoad 26/60 Superdex 200 pg column at a flow rate of 0.8 ml/min. In contrast to wild type sgp130Fc, CR5/18 eluted in a single peak after a low peak of aggregates of higher molecular weight (FIG. 2). In the first runs, samples of all fractions were obtained for PAGE analysis. Peak fractions were pooled, their protein concentrations were measured and set to 400-500 μg/ml in PBS, and single-use aliquots were frozen at −80° C. for long-term storage. Fractions and pool samples were analysed by native PAGE (7.5%) and subsequent silver or Coomassie staining.

As shown in FIG. 2, the amount of side products (aggregates) of CR5/18 is significantly reduced as compared to the parental compound sgp130Fc which was purified in a parallel experiment. Moreover, the elution of the desired product (CR5/18 dimer) is clearly separable from the impurity fractions (aggregates), which is not the case with wild type sgp130Fc. Thus, both yield (due to a higher proportion of the desired product) and quality of CR5/18 preparations are better than those of conventional sgp130Fc, leading to lower costs for the industrial production. These results indicate a clear improvement of CR5/18 over the parental sgp130Fc molecule.

EXAMPLE 2

Bioactivity of CR5/18 in a Standardized Cell Proliferation Assay (A) Material

The stably transfected B cell precursor cell line BAF3/gp130 and the designer cytokine Hyper-IL-6 were used. Culture medium components were purchased as follows: DMEM and PBS (PAA Laboratories; Cölbe, Germany), FBS (Biochrom; Berlin, Germany) and Trypsin/EDTA solution (Invitrogen; Karlsruhe, Germany). Interleukin-6 (IL-6) and soluble interleukin-6 receptor (sIL-6R) were purchased from BioSource (Solingen, Germany) and R&D Systems (Wiesbaden, Germany), respectively. The Cell Titer 96 Aqueous Non-Radioactive Cell Proliferation Assay (MTS) was obtained from Promega (Mannheim, Germany).

(B) Blockage of IL-6/sIL-6R-Induced BAF3/gp130 Cell Proliferation by sgp130Fc or CR5/18

BAF3/gp130 cells depend on the presence of the IL-6/sIL-6R complex in the culture medium for proliferation and viability. For maintenance, BAF3/gp130 cells were cultured at a density of less than $5\times10^5$ cells/mL in DMEM with 10% FBS and 10 ng/mL Hyper-IL-6 (a designer cytokine consisting of covalently linked IL-6 and sIL-6R; Fischer et al. 1997, Nat. Biotechnol. 15: 142-145). The 10 ng/mL Hyper-IL-6 could be replaced by 100 ng/mL IL-6 and 50 ng/mL sIL-6R. Cells were passaged twice a week. For assays, cells were washed twice in medium without Hyper-IL-6 (or IL-6/sIL-6R) and were then seeded at 5,000 cells/well in 96-well plates. CR5/18 or the parent compound sgp130Fc were added at various concentrations ranging from 20 μg/mL to 78 ng/mL (1:4 dilution series; FIG. 3). Subsequently, cells were incubated for 3 days in the presence of 100 ng/mL IL-6 and 50 ng/mL sIL-6R. Controls included unstimulated cells without and with the maximum concentration of CR5/18 or sgp130Fc as well as cells incubated with the stimulants IL-6 and sIL-6R only (FIG. 3).

(C) Results

The biological activity of CR5/18 or wild type sgp130Fc in the cell culture was measured by the reduction of the number of viable BAF3/gp130 cells (as determined by MTS substrate conversion) after 3 days. CR5/18 is more biologically active than wildtype sgp130Fc, reaching its $IC_{50}$ at a concentration of ca. 400 ng/mL where sgp130Fc ($IC_{50} \approx 800$ ng/mL) still shows no significant effect (FIG. 3). This indicates that CR5/18 could be used at about half the therapeutic concentration of the wildtype compound.

The invention claimed is:

1. A method of treating a subject having an inflammatory disease, comprising administering to the subject in an effective amount of a pharmaceutical composition comprising a polypeptide dimer capable of inhibiting activity of IL-6/sIL-6R complex and comprising two monomers, wherein each monomer comprises an extracellular domain of a gp 130 molecule fused to an Fc domain of an IgG1 protein, wherein each monomer comprises amino acids 23-844 of SEQ ID NO: 11, and wherein the inflammatory disease is Crohn's disease or ulcerative colitis.

2. The method of claim 1, wherein each monomer comprises an extracellular domain of the gp130 molecule fused directly to the Fc domain.

3. The method of claim 1, wherein each monomer comprises an extracellular domain of the gp130 molecule fused to the Fc domain via a flexible polypeptide linker.

4. The method of claim 3, wherein the linker comprises 2 to 50 amino acid residues independently selected from the group consisting of glycine, serine, asparagine, threonine and alanine.

5. The method of claim 1, wherein each of the monomers comprises one or more N-glycosylation sites between the extracellular domain of the gp130 molecule and the Fc domain.

6. The method of claim 1, wherein the monomers are linked to each other through a covalent bond, a flexible peptide linker or one or more disulfide bridges.

7. The method of claim 1, wherein at least one of the monomers is PEGylated.

8. The method of claim 1, wherein the two monomers are PEGylated.

9. The method of claim 1, wherein the pharmaceutical composition further comprises a pharmaceutically acceptable carrier.

* * * * *

SEQUENCE LISTING

```
<160> NUMBER OF SEQ ID NOS: 11

<210> SEQ ID NO 1
<211> LENGTH: 4
<212> TYPE: PRT
<213> ORGANISM: Homo Sapiens

<400> SEQUENCE: 1

Ala Glu Gly Ala
1
```

```
<210> SEQ ID NO 2
<211> LENGTH: 4
<212> TYPE: PRT
<213> ORGANISM: Homo Sapiens

<400> SEQUENCE: 2

Leu Leu Gly Gly
1

<210> SEQ ID NO 3
<211> LENGTH: 20
<212> TYPE: PRT
<213> ORGANISM: Homo Sapiens

<400> SEQUENCE: 3

Asp Lys Thr His Thr Cys Pro Pro Cys Pro Ala Pro Glu Ala Glu Gly
1               5                   10                  15

Ala Pro Ser Val
            20

<210> SEQ ID NO 4
<211> LENGTH: 20
<212> TYPE: PRT
<213> ORGANISM: Homo Sapiens

<400> SEQUENCE: 4

Asp Lys Thr His Thr Cys Pro Pro Cys Pro Ala Pro Glu Leu Leu Gly
1               5                   10                  15

Gly Pro Ser Val
            20

<210> SEQ ID NO 5
<211> LENGTH: 20
<212> TYPE: PRT
<213> ORGANISM: Homo Sapiens
<220> FEATURE:
<221> NAME/KEY: Mutagen
<222> LOCATION: (14)..(14)
<223> OTHER INFORMATION: XAA is Ala or Phe
<220> FEATURE:
<221> NAME/KEY: Mutagen
<222> LOCATION: (15)..(15)
<223> OTHER INFORMATION: Xaa is Asp or Glu

<400> SEQUENCE: 5

Asp Lys Thr His Thr Cys Pro Pro Cys Pro Ala Pro Glu Xaa Xaa Gly
1               5                   10                  15

Ala Pro Ser Val
            20

<210> SEQ ID NO 6
<211> LENGTH: 20
<212> TYPE: PRT
<213> ORGANISM: artificial
<220> FEATURE:
<223> OTHER INFORMATION: mutant 1; hinge region IgG1

<400> SEQUENCE: 6

Asp Lys Thr His Thr Cys Pro Pro Cys Pro Ala Pro Glu Ala Glu Gly
1               5                   10                  15

Ala Pro Ser Val
            20
```

<210> SEQ ID NO 7
<211> LENGTH: 20
<212> TYPE: PRT
<213> ORGANISM: artificial
<220> FEATURE:
<223> OTHER INFORMATION: mutant 2; hinge region of IgG1

<400> SEQUENCE: 7

Asp Lys Thr His Thr Cys Pro Pro Cys Pro Ala Pro Glu Ala Asp Gly
1               5                   10                  15

Ala Pro Ser Val
            20

<210> SEQ ID NO 8
<211> LENGTH: 20
<212> TYPE: PRT
<213> ORGANISM: artificial
<220> FEATURE:
<223> OTHER INFORMATION: mutant 3; hinge region of IgG1

<400> SEQUENCE: 8

Asp Lys Thr His Thr Cys Pro Pro Cys Pro Ala Pro Glu Phe Glu Gly
1               5                   10                  15

Ala Pro Ser Val
            20

<210> SEQ ID NO 9
<211> LENGTH: 20
<212> TYPE: PRT
<213> ORGANISM: artificial
<220> FEATURE:
<223> OTHER INFORMATION: mutant 4; hinge region of IgG1

<400> SEQUENCE: 9

Asp Lys Thr His Thr Cys Pro Pro Cys Pro Ala Pro Glu Phe Asp Gly
1               5                   10                  15

Ala Pro Ser Val
            20

<210> SEQ ID NO 10
<211> LENGTH: 2535
<212> TYPE: DNA
<213> ORGANISM: Homo Sapiens

<400> SEQUENCE: 10

```
atgctgacac tgcagacatg gctggtgcag gccctgttta tctttctgac caccgagtct      60
acaggagagc tgctggatcc ttgcggctat atctcccctg agtctcctgt ggtgcagctg     120
cattctaact tcaccgccgt gtgtgtgctg aaggaaaagt gcatggacta cttccacgtg     180
aacgccaact acatcgtgtg gaaaaccaac cacttcacca tccccaagga gcagtacacc     240
atcatcaacc ggaccgcttc ttctgtgacc ttcaccgata tcgcctccct gaatatccag     300
ctgacctgca acatcctgac ctttggacag ctggagcaga atgtgtacgg catcaccatc     360
atctctggcc tgcctccaga gaagcctaag aacctgtcct gcatcgtgaa tgagggcaag     420
aagatgaggt gtgagtggga tgcggcagag agacacatc tggagaccaa cttcaccctg     480
aagtctgagt gggccaccca caagtttgcc gactgcaagg ccagagagag tacccctacc     540
tcttgcaccg tggactactc caccgtgtac ttcgtgaaca tcgaggtgtg ggtggaggct     600
gagaatgctc tggcaaggt gacctctgac cacatcaact tcgaccccgt gtacaaggtg     660
aagcctaacc ctcctcacaa cctgtccgtg atcaactctg aggagctgtc ctctatcctg     720
```

-continued

| | |
|---|---|
| aagctgacct ggaccaaccc ttccatcaag tccgtgatca tcctgaagta caacatccag | 780 |
| tacaggacca aggatgcttc tacctggtct cagatccctc ctgaggatac cgcttccacc | 840 |
| agatccagct tcacagtgca ggacctgaag ccttttaccg agtacgtgtt caggatccgg | 900 |
| tgcatgaagg aggatggcaa gggctattgg tctgactggt ctgaggaggc ttctggcatc | 960 |
| acctacgagg acagaccttc taaggcccct agcttctggt acaagatcga cccttctcac | 1020 |
| acccagggct atagaacagt gcagctggtg tggaaaaccc tgcctccatt cgaggctaat | 1080 |
| ggcaagatcc tggactatga ggtgaccctg accagatgga agtctcacct gcagaactac | 1140 |
| accgtgaacg ctaccaagct gaccgtgaac ctgaccaacg atagatacct ggctaccctg | 1200 |
| accgtgagaa atctggtggg caagtctgat gctgctgtgc tgaccatccc tgcctgtgat | 1260 |
| tttcaggcta cccaccctgt gatggatctg aaggccttcc ccaaggataa catgctgtgg | 1320 |
| gtggagtgga caacacctag agagtccgtg aagaagtaca tcctggagtg gtgcgtgctg | 1380 |
| tctgataagg ccccttgcat cacagattgg cagcaggagg atggcaccgt gcatagaacc | 1440 |
| tacctgagag gcaatctggc cgagtctaag tgctatctga tcaccgtgac ccctgtgtat | 1500 |
| gctgatggac ctggctctcc tgagtctatc aaggcctacc tgaagcaggc tcctccatct | 1560 |
| aagggaccta ccgtgaggac aaagaaggtg ggcaagaacg aggctgtgct ggagtgggat | 1620 |
| cagctgcctg tggatgtgca aacggcttc atccggaact acaccatctt ctaccggacc | 1680 |
| atcatcggca tgagaccgc cgtgaacgtg gattcttccc acaccgagta cacactgtcc | 1740 |
| tctctgacct ctgacaccct gtacatggtg agaatggccg cttataccga tgagggcggc | 1800 |
| aaggatggac ctgagttcac cttcaccacc cctaagttcg cccagggcga ggacaagacc | 1860 |
| cacacctgtc ctccttgtcc tgctcctgag gctgagggcg ctccttctgt gtttctgttc | 1920 |
| cccccaaagc ctaaggatac cctgatgatc tccagaaccc ctgaggtgac atgtgtggtg | 1980 |
| gtggatgtgt ctcatgagga ccccgaggtg aagttcaact ggtacgtgga tggcgtggag | 2040 |
| gtgcacaatg ctaagaccaa gcctagggag gagcagtaca actccaccta cagagtggtg | 2100 |
| tctgtgctga cagtgctgca tcaggattgg ctgaacggca aggagtacaa gtgcaaggtg | 2160 |
| tccaacaagg ctctgcctgc tcctatcgaa aagaccatct ccaaggctaa gggacagcct | 2220 |
| agagagcctc aggtgtacac actgcctcca tctagggagg agatgaccaa gaatcaggtg | 2280 |
| tccctgacct gtctggtgaa gggcttctac ccttctgata tcgctgtgga gtgggagtct | 2340 |
| aatggccagc ccgagaacaa ttacaagacc accctcctg tgctggattc tgacggctcc | 2400 |
| ttcttcctgt actccaaact gaccgtggac aagtctagat ggcagcaggg caacgtgttc | 2460 |
| tcttgttccg tgatgcacga ggctctgcac aatcactata cccagaagtc cctgtctctg | 2520 |
| tctcctggca agtga | 2535 |

<210> SEQ ID NO 11
<211> LENGTH: 844
<212> TYPE: PRT
<213> ORGANISM: Homo Sapiens

<400> SEQUENCE: 11

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
                20                  25                  30

Pro Glu Ser Pro Val Val Gln Leu His Ser Asn Phe Thr Ala Val Cys
        35                  40                  45

```
Val Leu Lys Glu Lys Cys Met Asp Tyr Phe His Val Asn Ala Asn Tyr
    50              55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
                100                 105                 110

Gln Asn Val Tyr Gly Ile Thr Ile Ser Gly Leu Pro Pro Glu Lys
                115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
                180                 185                 190

Asn Ile Glu Val Trp Val Glu Ala Glu Asn Ala Leu Gly Lys Val Thr
                195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
                260                 265                 270

Pro Pro Glu Asp Thr Ala Ser Thr Arg Ser Ser Phe Thr Val Gln Asp
    275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
                340                 345                 350

Thr Leu Pro Pro Phe Glu Ala Asn Gly Lys Ile Leu Asp Tyr Glu Val
    355                 360                 365

Thr Leu Thr Arg Trp Lys Ser His Leu Gln Asn Tyr Thr Val Asn Ala
    370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
                420                 425                 430

Phe Pro Lys Asp Asn Met Leu Trp Val Glu Trp Thr Thr Pro Arg Glu
    435                 440                 445

Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
```

```
465                 470                 475                 480
Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
            515                 520                 525

Lys Val Gly Lys Asn Glu Ala Val Leu Glu Trp Asp Gln Leu Pro Val
        530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
                580                 585                 590

Ala Ala Tyr Thr Asp Glu Gly Gly Lys Asp Gly Pro Glu Phe Thr Phe
            595                 600                 605

Thr Thr Pro Lys Phe Ala Gln Gly Glu Asp Lys Thr His Thr Cys Pro
            610                 615                 620

Pro Cys Pro Ala Pro Glu Ala Glu Gly Ala Pro Ser Val Phe Leu Phe
625                 630                 635                 640

Pro Pro Lys Pro Lys Asp Thr Leu Met Ile Ser Arg Thr Pro Glu Val
                645                 650                 655

Thr Cys Val Val Val Asp Val Ser His Glu Asp Pro Glu Val Lys Phe
                660                 665                 670

Asn Trp Tyr Val Asp Gly Val Glu Val His Asn Ala Lys Thr Lys Pro
            675                 680                 685

Arg Glu Glu Gln Tyr Asn Ser Thr Tyr Arg Val Val Ser Val Leu Thr
        690                 695                 700

Val Leu His Gln Asp Trp Leu Asn Gly Lys Glu Tyr Lys Cys Lys Val
705                 710                 715                 720

Ser Asn Lys Ala Leu Pro Ala Pro Ile Glu Lys Thr Ile Ser Lys Ala
                725                 730                 735

Lys Gly Gln Pro Arg Glu Pro Gln Val Tyr Thr Leu Pro Pro Ser Arg
            740                 745                 750

Glu Glu Met Thr Lys Asn Gln Val Ser Leu Thr Cys Leu Val Lys Gly
            755                 760                 765

Phe Tyr Pro Ser Asp Ile Ala Val Glu Trp Glu Ser Asn Gly Gln Pro
            770                 775                 780

Glu Asn Asn Tyr Lys Thr Thr Pro Pro Val Leu Asp Ser Asp Gly Ser
785                 790                 795                 800

Phe Phe Leu Tyr Ser Lys Leu Thr Val Asp Lys Ser Arg Trp Gln Gln
                805                 810                 815

Gly Asn Val Phe Ser Cys Ser Val Met His Glu Ala Leu His Asn His
            820                 825                 830

Tyr Thr Gln Lys Ser Leu Ser Leu Ser Pro Gly Lys
            835                 840
```